(12) United States Patent
Redl et al.

(10) Patent No.: US 7,537,174 B2
(45) Date of Patent: May 26, 2009

(54) HAND TRIGGERED TISSUE SEALANT SPRAY APPARATUS AND SYSTEM

(75) Inventors: Heinz Redl, Vienna (AT); Zafar Khakpour, Vienna (AT); Scott R. Ariagno, Lemont, IL (US); Andreas Kellner, Vienna (AT); Lillian G. Zakarija, Chicago, IL (US)

(73) Assignees: Baxter International Inc., Deerfield, IL (US); Baxter Healthcare S.A., Wallisellen, Zurich (CH)

( * ) Notice: Subject to any disclaimer, the term of this patent is extended or adjusted under 35 U.S.C. 154(b) by 368 days.

(21) Appl. No.: 11/331,243

(22) Filed: Jan. 12, 2006

(65) Prior Publication Data
US 2006/0191962 A1    Aug. 31, 2006

Related U.S. Application Data

(60) Provisional application No. 60/643,368, filed on Jan. 12, 2005.

(51) Int. Cl.
| A62C 13/62 | (2006.01) |
| A62C 5/00 | (2006.01) |
| B05B 9/04 | (2006.01) |
| B05B 11/02 | (2006.01) |
| F23D 11/10 | (2006.01) |
| B67D 5/52 | (2006.01) |

(52) U.S. Cl. ............... 239/321; 239/306; 239/311; 239/418; 222/137; 222/391

(58) Field of Classification Search ........... 239/302, 239/303, 304, 306, 310, 311, 320, 321, 322, 239/372, 418, 419.3; 604/82, 191, 289; 222/137, 222/145.5, 327, 391
See application file for complete search history.

(56) References Cited

U.S. PATENT DOCUMENTS 5,582,596 A * 12/1996 Fukunaga et al. ............ 604/191

(Continued)

FOREIGN PATENT DOCUMENTS

EP    0 634 140 A1    1/1995

(Continued)

OTHER PUBLICATIONS

ISR for PCT/US06/000970, Jun. 27, 2006, Baxter International.

*Primary Examiner*—Len Tran
*Assistant Examiner*—Ryan Reis
(74) *Attorney, Agent, or Firm*—Jeffrey C. Nichols; Austin J. Foley; Joseph P. Reagen

(57) ABSTRACT

The present invention is generally directed to various structures for applying a sealant to a work surface. In one aspect of the invention, a sealant applicator assembly is provided for use with an apparatus of the type having an elongated body defining an interior bore and having a piston movably positioned in the bore and a pusher member operatively associated with the piston. The assembly comprises a spray adaptor adapted to communicate with the bore of the body and defining a distal outlet. A first gas passageway is cooperatively associated with the distal outlet and configured to direct gas to create a spray discharge of the sealant. An actuating member is adapted to be cooperative associated with a pusher member to eject sealant through the distal outlet and is operative to simultaneously actuate a supply of gas to the first gas passageway for creating a spray discharge of sealant.

17 Claims, 11 Drawing Sheets

U.S. PATENT DOCUMENTS

| | | |
|---|---|---|
| 5,605,541 A | 2/1997 | Holm |
| 5,665,067 A * | 9/1997 | Linder et al. .................. 604/82 |
| 5,759,169 A | 6/1998 | Marx |
| 5,759,171 A | 6/1998 | Coelho et al. |
| 5,887,755 A | 3/1999 | Hood, III |
| 5,971,956 A | 10/1999 | Epstein |
| 6,007,515 A * | 12/1999 | Epstein et al. ................ 604/82 |
| 6,047,861 A | 4/2000 | Vidal et al. |
| 6,059,749 A | 5/2000 | Marx |
| 6,206,905 B1 | 3/2001 | Holm et al. |
| 6,331,172 B1 | 12/2001 | Epstein et al. |
| 6,432,084 B1 | 8/2002 | Levinson et al. |
| 6,454,786 B1 * | 9/2002 | Holm et al. .................. 606/214 |
| 6,461,325 B1 * | 10/2002 | Delmotte et al. .............. 604/82 |
| 6,461,361 B1 | 10/2002 | Epstein |
| 6,464,663 B1 * | 10/2002 | Zinger .......................... 604/82 |
| 6,471,667 B1 * | 10/2002 | Epstein ........................ 604/28 |
| 6,540,716 B1 | 4/2003 | Holm |
| 6,565,539 B1 * | 5/2003 | Zinger et al. ................ 604/191 |
| 6,585,696 B2 | 7/2003 | Petersen et al. |
| 6,613,020 B1 | 9/2003 | Holm et al. |
| 6,733,472 B1 | 5/2004 | Epstein et al. |
| 6,770,050 B2 | 8/2004 | Epstein |
| 6,852,099 B2 | 2/2005 | Redl et al. |
| 6,860,870 B2 | 3/2005 | Pichon et al. |
| 6,874,657 B2 | 4/2005 | Metzner et al. |
| 6,884,230 B1 | 4/2005 | Epstein et al. |

FOREIGN PATENT DOCUMENTS

| | | |
|---|---|---|
| WO | WO 95/31138 A1 | 11/1995 |
| WO | WO 96/39212 A2 | 12/1996 |
| WO | WO 97/20585 A1 | 6/1997 |
| WO | WO 03/068296 A2 | 8/2003 |

* cited by examiner

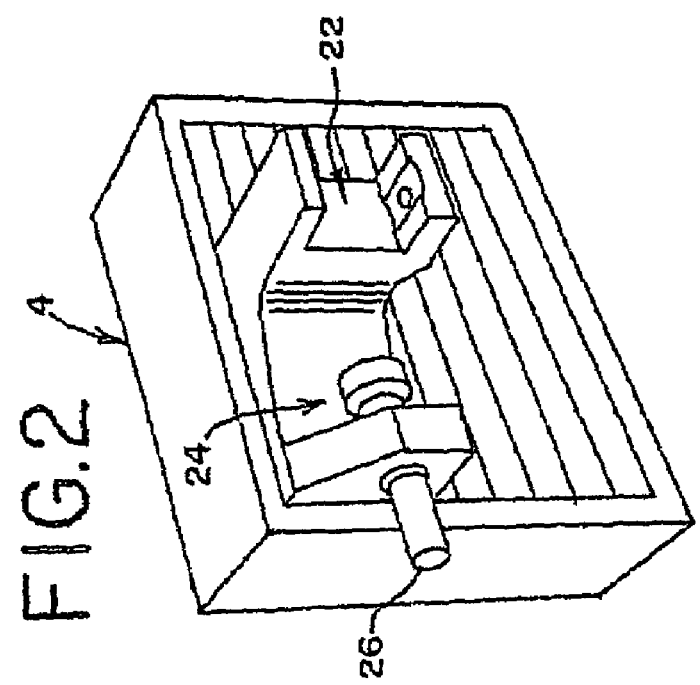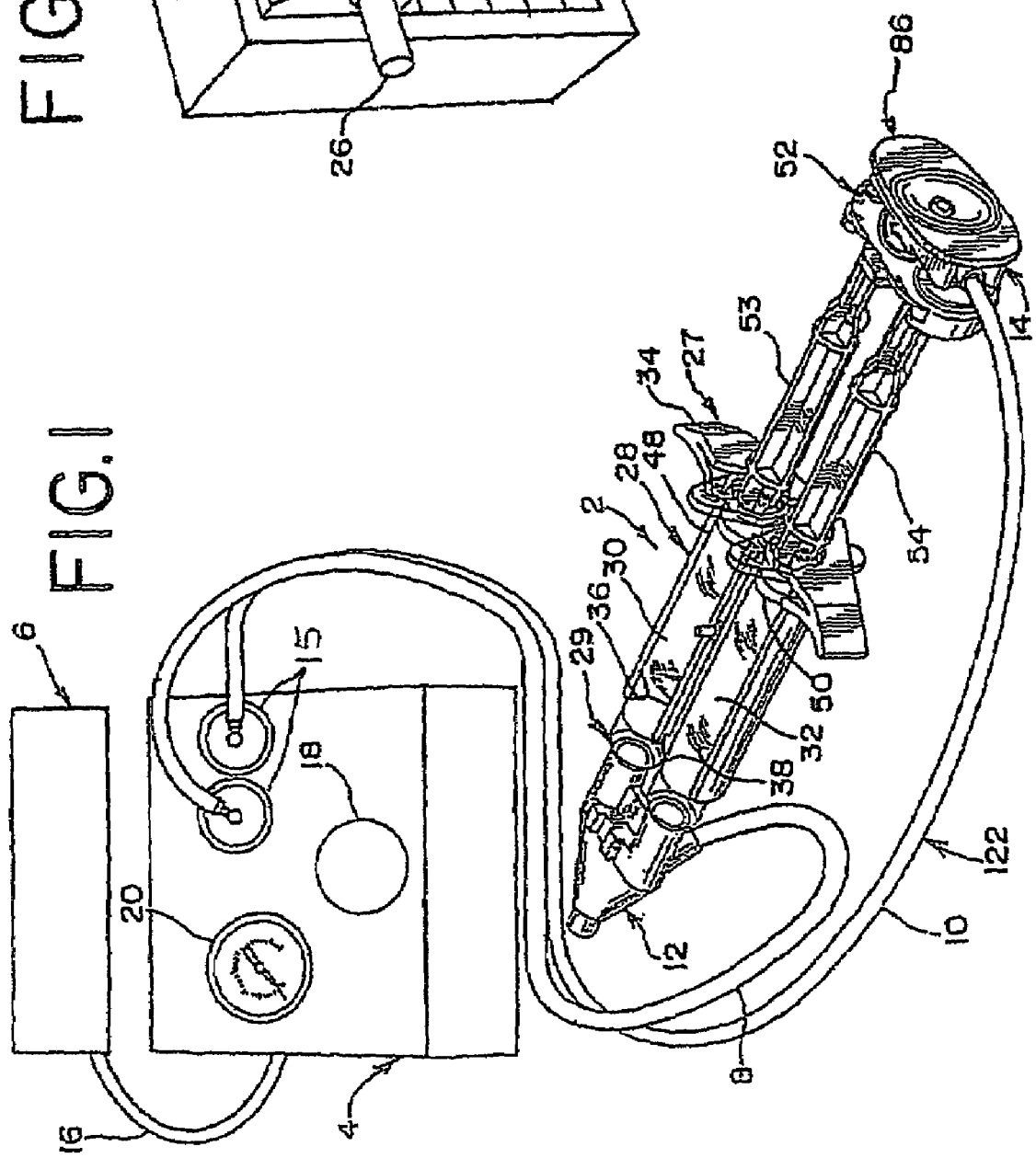

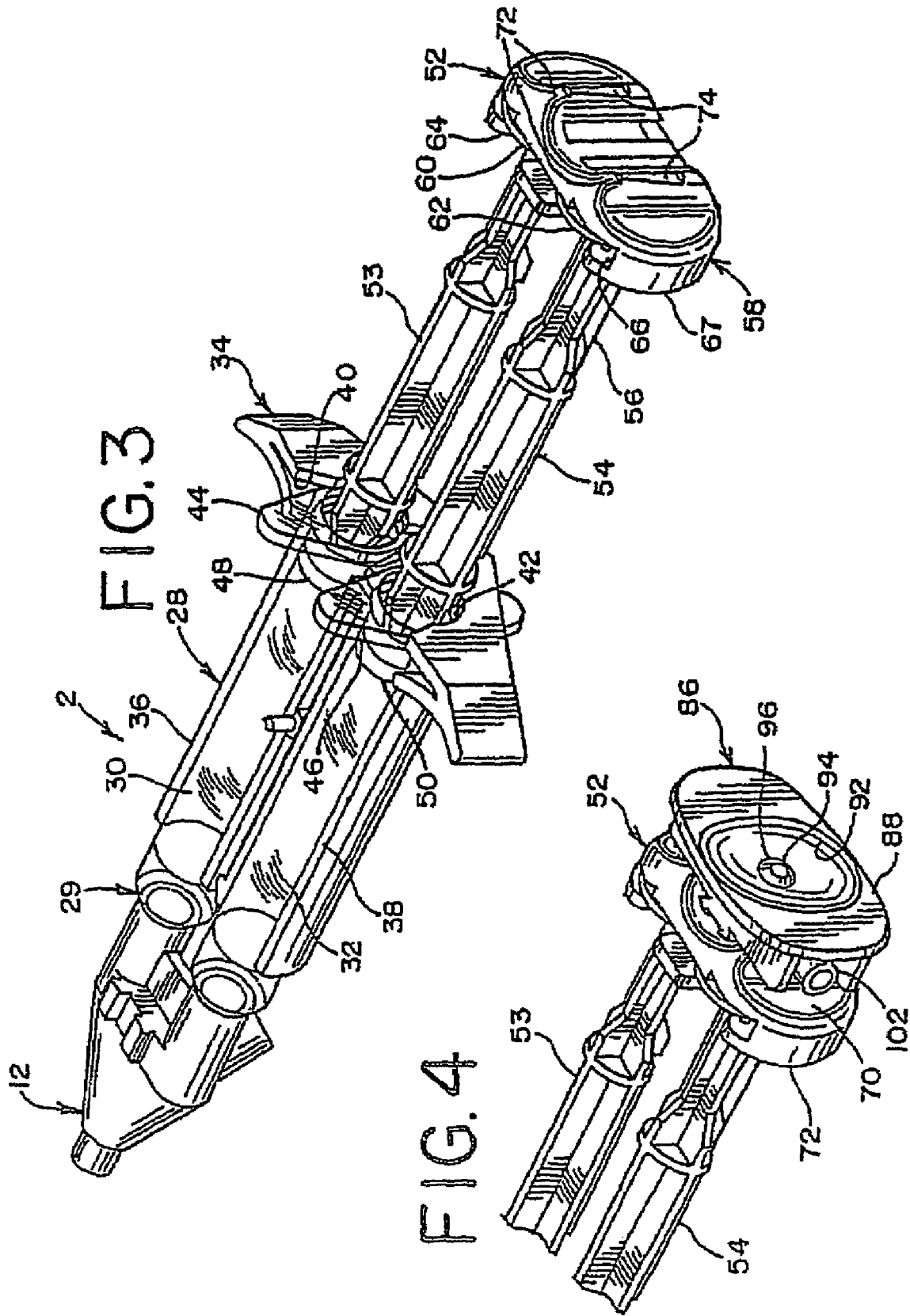

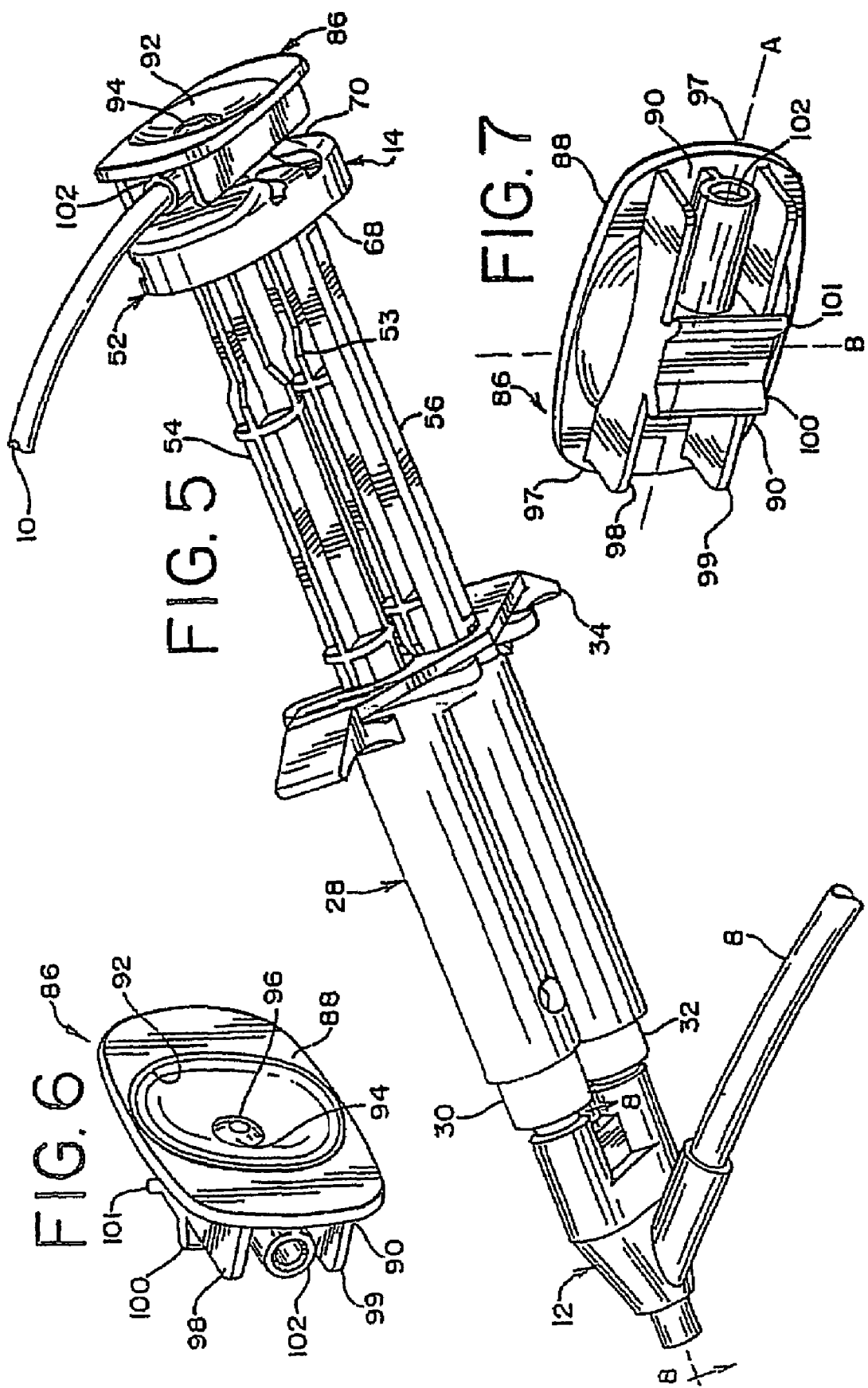

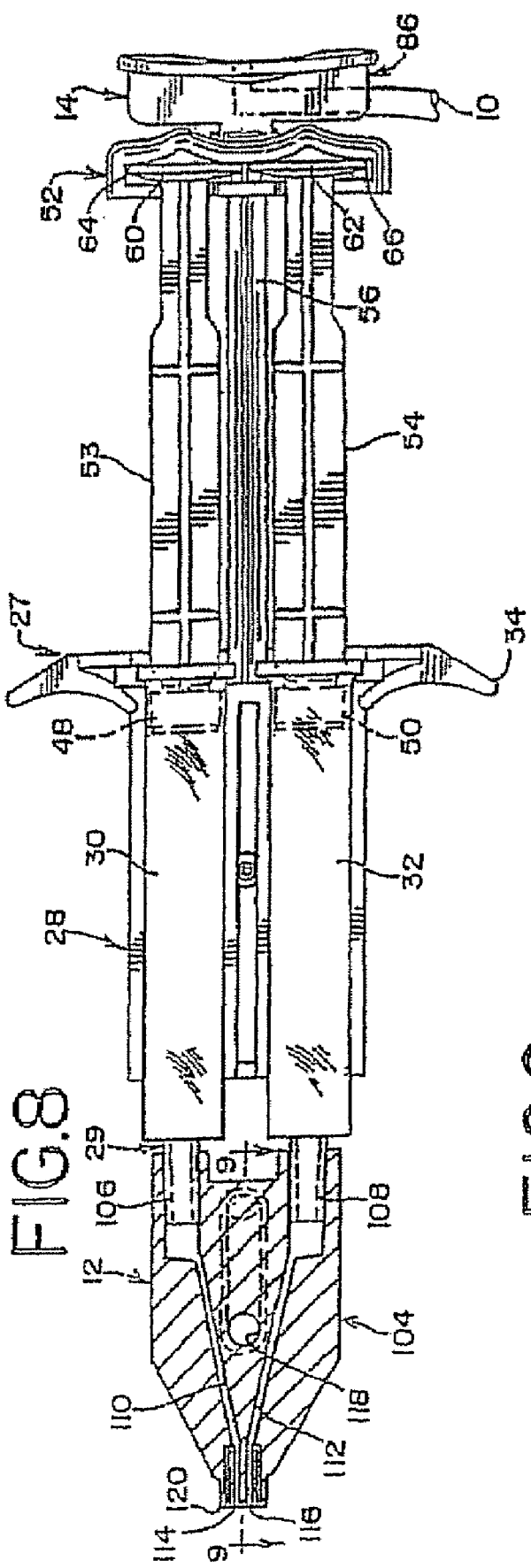
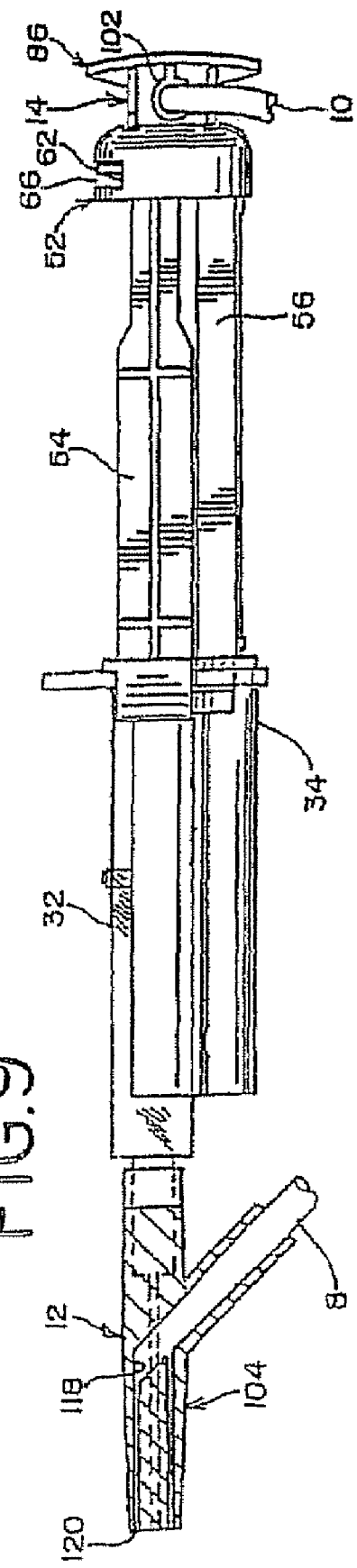

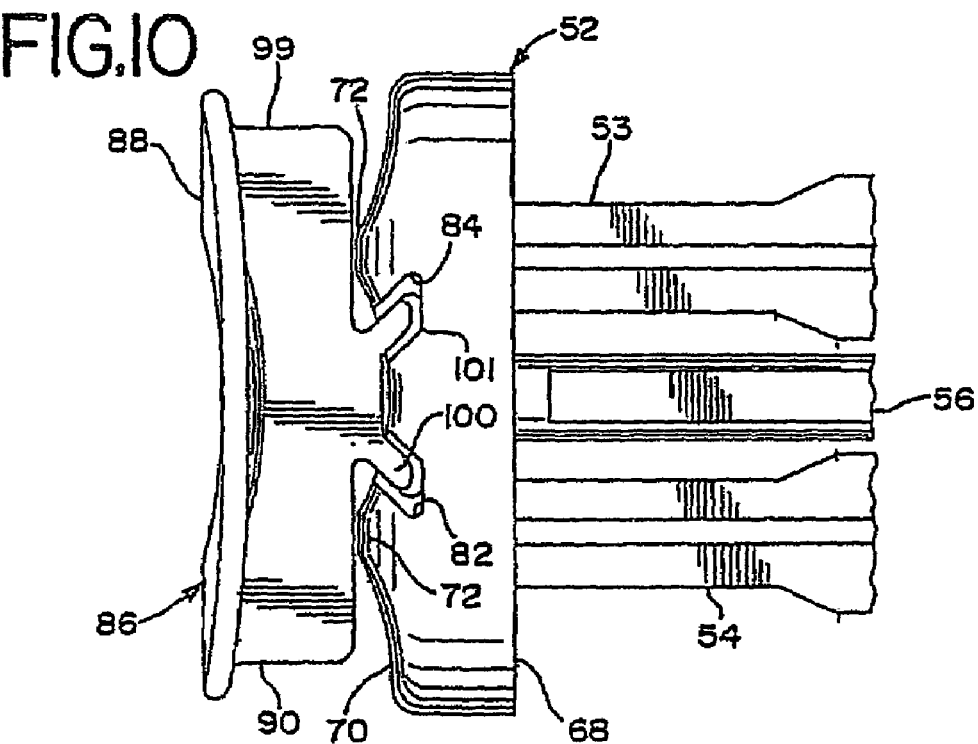
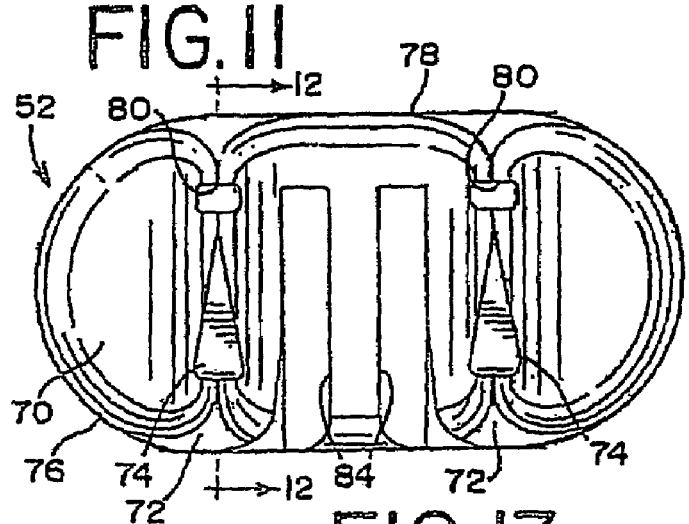
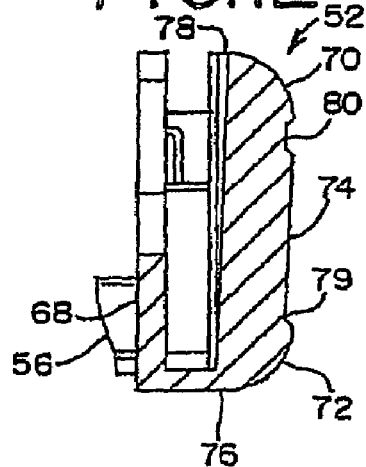
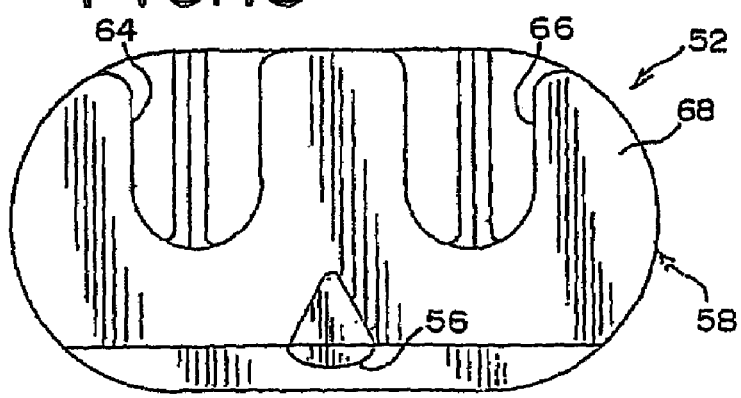

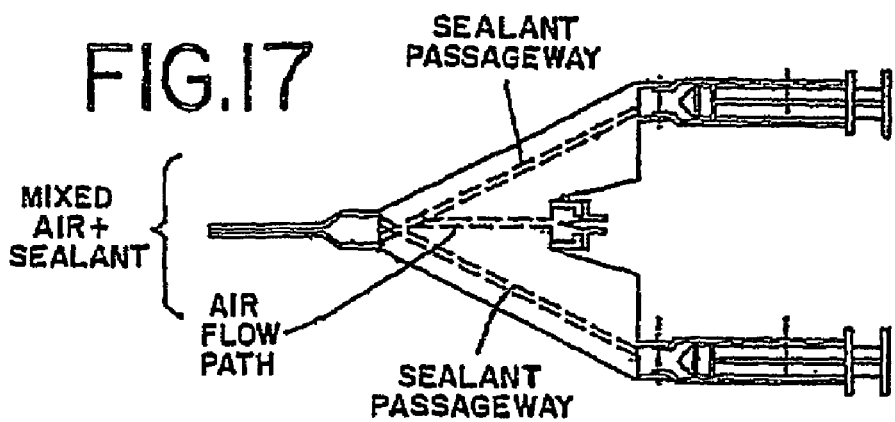
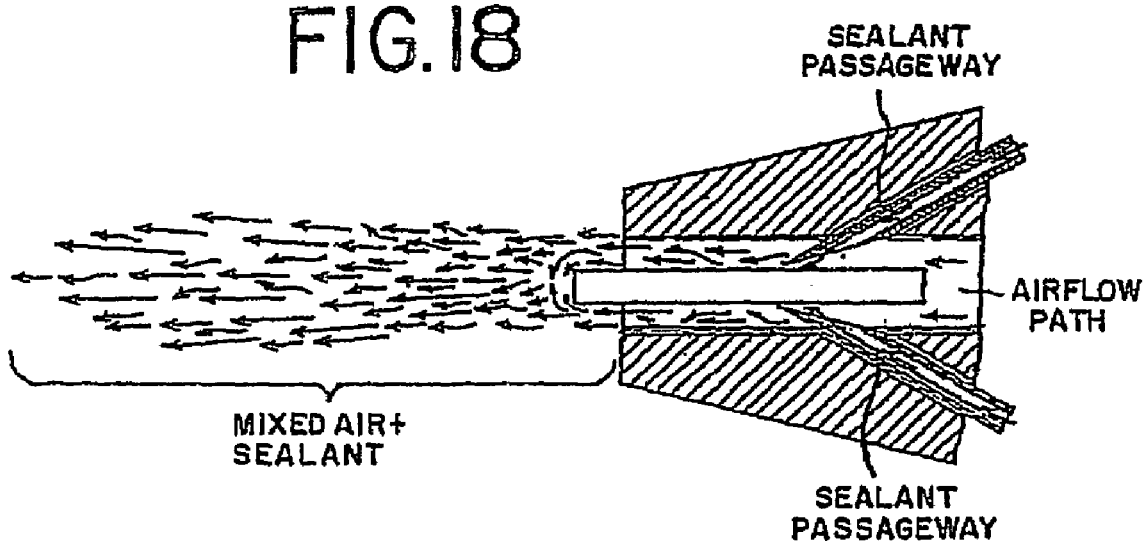
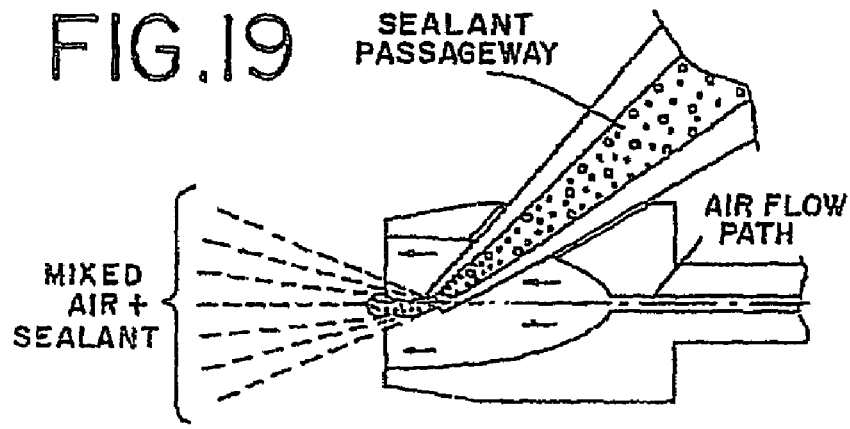

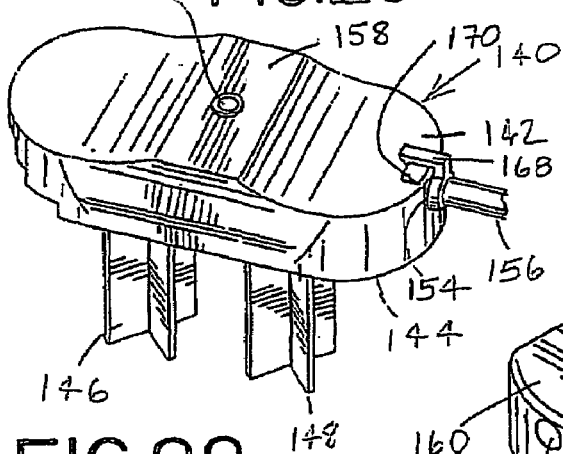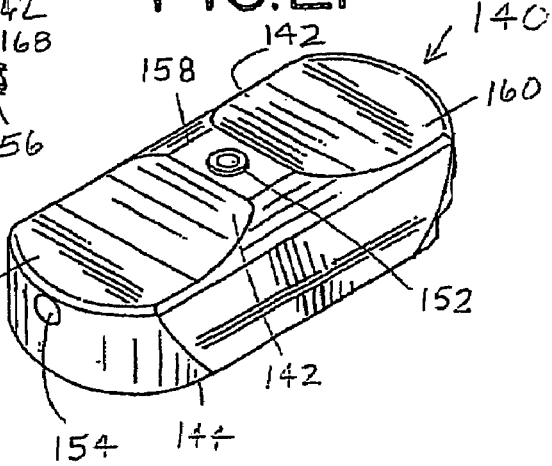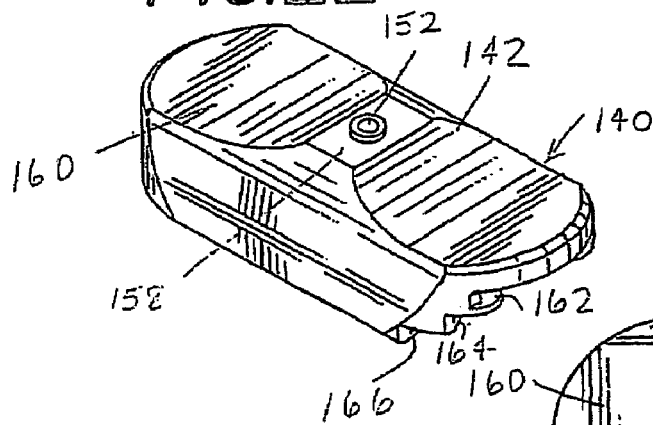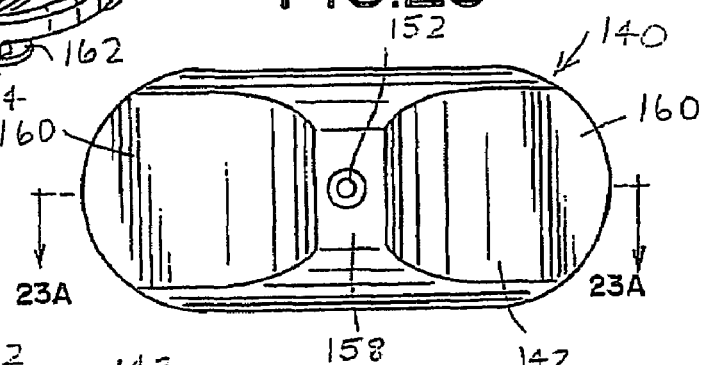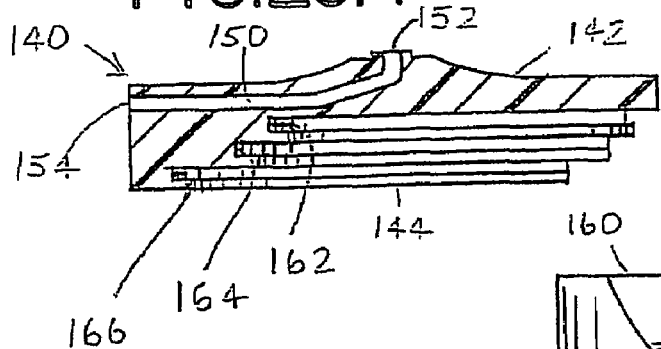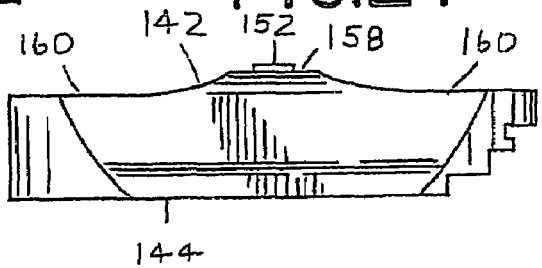

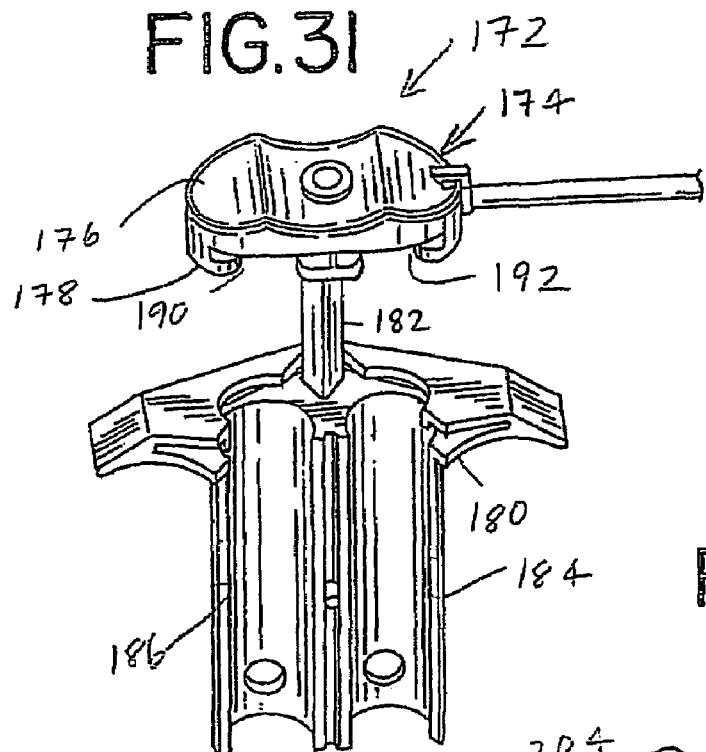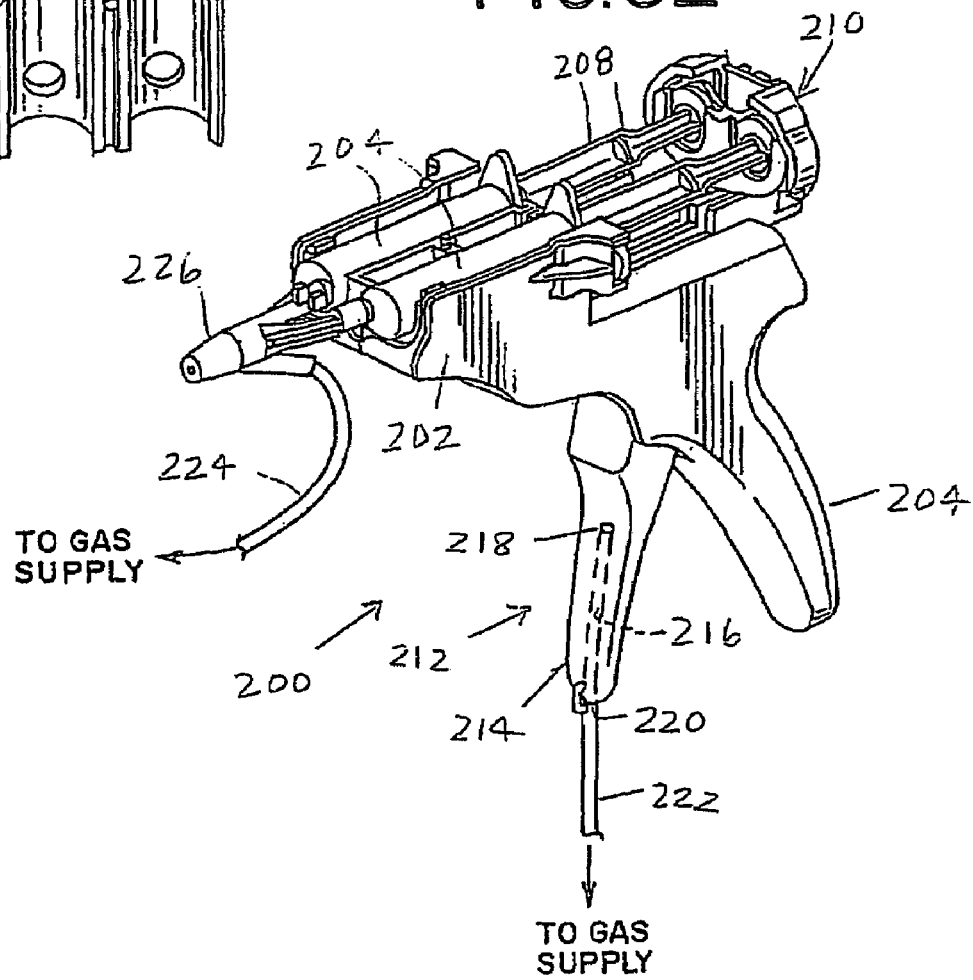

HAND TRIGGERED TISSUE SEALANT SPRAY APPARATUS AND SYSTEM

CROSS REFERENCE TO RELATED APPLICATION

This application claims priority to U.S. Provisional Application Ser. No. 60/643,368, filed Jan. 12, 2005, which is incorporated by reference herein.

BACKGROUND

This invention relates to a system and apparatus for applying tissue sealant, such as tissue sealant, to a work surface, such as biological tissue.

Mixing and/or applying sealant to work surfaces has application in a variety of settings. In the medical field, sealant in the form of tissue sealants have been applied to human and animal tissue, for example, to seal or repair tissue at a surgical or wound site, to stop bleeding, seal wounds, treat burns or skin grafts and a variety of other purposes.

In the medical field, tissue sealant has typically been applied by a syringe-type applicator that ejects tissue sealant directly onto the tissue. Examples of such applicators are shown in U.S. Pat. Nos. 4,846,405, 5,582,596, 5,665,067, 6,461,361 and 6,585,696, and PCT Publication No. WO 96/39212, all of which are incorporated herein by reference. Further examples of such applicators also are sold under the Tissomat and Duploject trademarks, which are marketed by Baxter A G.

The tissue sealant employed in treating biological tissue is typically made of one or more components, such as biocompatible compounds that can be absorbed by the body and do not require later removal from the patient. One example of a known tissue sealant is made of fibrinogen and thrombin. The tissue sealant may be contained in more than one container which can be mixed into an adhesive combination upon ejection from the tissue sealant applicator. For example, the components may exit from two separate outlets positioned in proximity with one another so that these components are mixed to create an adhesive tissue sealant upon ejection from the applicator.

Tissue sealant applicators also may provide tissue sealant that is atomized by means of pressurized, sterile gas such as, for example, air, to form a spray which is a combination of tissue sealant and a sterile gas or air. The applicator is connected to an air or gas source by tubing that supplies the gas or air to the distal end of the applicator in the vicinity of the outlets of the one or more tissue sealant components. For example, gas may communicate with one or more of the tissue sealant components within a mixing area defined by the applicator. Alternatively, the gas may mix with the tissue sealant components after ejection from the applicator. In the latter scheme, the gas or air outlet preferably is located in close proximity to the outlets of one or more of the tissue sealant components and may, for example, be in the form of an annular shaped outlet which surrounds at least one of the tissue sealant component outlets. The result is that the tissue sealant discharges in the form of an aerosol or spray.

The supply of gas or air is preferably coordinated so that, for example, gas is essentially simultaneously supplied to the applicator upon ejection of tissue sealant. However, synchronizing the timing of this supply with the ejection of tissue sealant or its components has proven awkward and difficult, particularly where multiple tissue sealant components are used.

Conventional tissue sealant applicators have relied on the user, such as a surgeon or hospital staff member, to simultaneously activate the supply of gas with the ejection of tissue sealant with separate motions. For example, the user is required to manually turn on and off the supply of gas, such as by foot actuation, in addition to the separate movement required to manually eject tissue sealant or components, such as, for example, by pressing on a syringe plunger or the like. It has proven difficult for the user to coordinate the timing of these two separate motions. Therefore, it is desired to provide a tissue sealant applicator which simplifies activation of a spray discharge of tissue sealant and which further provides a reliable and continuous spray discharge of tissue sealant.

SUMMARY OF THE INVENTION

The present invention is generally directed to a system and apparatus for applying or, an apparatus for use in applying, sealant, such as tissue sealant, to a work surface, such as biological tissue, in which a supply of gas may be reliably actuated essentially simultaneously with the ejection of the sealant.

In accordance with one aspect of the present invention, an apparatus is provided that comprises an elongated body defining an interior bore for containing sealant, for example, tissue sealant, and having proximal and distal ends. A piston is movably positioned in the bore. The apparatus further comprises a distal outlet communicating with the bore. A first gas passageway is cooperatively associated with the distal outlet and is configured to direct gas to create a spray discharge of sealant. An actuating member is cooperatively associated with the piston for moving the piston toward the distal end of the body to eject sealant through the distal outlet and operative to simultaneously actuate a supply of gas to the first gas passageway to create a spray discharge of sealant for application to the work surface, for example, biological tissue.

In accordance with another aspect of the present invention, a sealant applicator assembly is provided for use with an apparatus of the type having an elongated body defining an interior bore for containing sealant, for example, tissue sealant, and having proximal and distal ends. The apparatus further includes a piston movably positioned in the bore and a pusher member operatively associated with the piston and extending through the proximal end of the bore. The sealant applicator assembly comprises a spray adaptor which is adapted to communicate with the bore of the body and defines a distal outlet. The sealant applicator assembly further comprises a first gas passageway which is cooperatively associated with the distal outlet and is configured to direct gas to create a spray discharge of the sealant. An actuating member is adapted to be cooperatively associated with the pusher member for moving the piston toward the distal end of the body to eject sealant through the distal outlet and operative to simultaneously actuate a supply of gas to the first gas passageway for creating a spray discharge of sealant.

In accordance with a further aspect of the present invention, a control unit is provided for use with an apparatus of the type comprising an elongated body defining an interior bore for containing sealant, for example, tissue sealant, and having proximal and distal ends. The apparatus further includes a piston movably positioned in the bore and a distal outlet communicating with the bore. A first gas passageway is cooperatively associated with the distal outlet and is configured to direct gas to create a spray discharge of sealant. An actuating member is cooperatively associated with the piston. The control unit is operable upon receipt of a control signal from the apparatus to activate a flow of gas suitable for communication with the first gas passageway to create a spray discharge of sealant.

In a yet further aspect of the present invention, a system is provided that comprises an apparatus and a gas supply source. The apparatus comprises an elongated body defining an interior bore for containing sealant, for example, a tissue sealant, and having proximal and distal ends. A piston is movably positioned in the bore. The apparatus further comprises a distal outlet communicating with the bore. A first gas passageway is cooperatively associated with the distal outlet and is configured to direct gas to create a spray discharge of sealant. An actuating member is cooperatively associated with the piston for moving the piston toward the distal end of the body to eject sealant through the distal outlet and operative to simultaneously actuate a supply of gas to the first gas passageway to create a spray discharge of sealant for application to a work surface, for example, biological tissue. The gas supply communicates with the first gas passageway. The system further provides that the actuating member is operatively connected to the gas supply source to at least selectively actuate the flow of gas through the first gas passageway to create a spray discharge of sealant for application to the work surface.

In accordance with an additional aspect of the present invention, an applicator assembly is provided for being cooperatively associated with an apparatus of the type having an elongated body defining an interior bore for containing sealant and having proximal and distal ends. The apparatus further includes a piston movably positioned in the bore, and a pusher member operatively associated with the piston extending through the proximal end of the bore. The applicator assembly also is provided for being cooperatively associated with a gas supplying device adapted to controllably supply a pressurized source of gas through a first gas outlet and also having an input to receive a supply signal and control the supply of the source of gas in at least partial dependence on the signal. The applicator assembly further provides for use by a user to supply a sealant to a work surface. Such applicator assembly comprises a spray adaptor adapted to communicate with the bore of the body and defining a distal outlet. Such applicator assembly also comprises a first gas passageway cooperatively associated with the distal outlet. The first gas passageway is configured to direct gas to create a spray discharge of the sealant. Such applicator assembly further comprises tubing in fluid communication with the first gas passageway and adapted to be placed in fluid communication with the first gas outlet. An actuating member is adapted to be cooperatively associated with the pusher member. The actuating member is also configured to generate the supply signal during movement of the pusher such that gas is supplied from the first gas outlet in at least partial dependence on the signal.

In accordance with another additional aspect of the present invention, an applicator assembly is provided for being cooperatively associated with an apparatus of the type having an elongated body defining an interior bore for containing sealant and having proximal and distal ends, a piston movably positioned in the bore, and a pusher member operatively associated with the piston extending through the proximal end of the bore. The applicator assembly is also provided to be for use by a user to supply a sealant to a work surface. Such applicator assembly comprises a gas supplying device adapted to controllably supply a pressurized source of gas through a first gas outlet and also having an input to receive a supply signal and control the supply of the source of gas in at least partial dependence on the signal. Such applicator assembly also comprises a spray adaptor adapted to communicate with the bore of the body and defining a distal outlet. Such applicator assembly further comprises a first gas passageway cooperatively associated with the distal outlet. The first gas passageway is configured to direct gas to create a spray discharge of the sealant. Tubing is in fluid communication with the first gas passageway and is adapted to be placed in fluid communication with the first gas outlet. An actuating member is adapted to be cooperatively associated with the pusher member. Such actuating member is configured to generate the supply signal during movement of the pusher such that gas is supplied from the first gas outlet in at least partial dependence on the signal.

In accordance with a further additional aspect of the present invention, an applicator assembly is provided for use by a user to supply a sealant to a work surface. Such applicator assembly comprises a first apparatus comprising an elongated body defining an interior bore for containing sealant and having proximal and distal ends. A piston is movably positioned in the bore, and a pusher member operatively associated with the piston extending through the proximal end of the bore. Such applicator assembly also comprises a gas supplying device having a first gas outlet, a supply signal input to receive a supply signal, a switch to actuate a flow of gas to the first gas outlet, and a control mechanism to cooperatively associate the switch and a signal supplied to the supply signal input. Such applicator assembly further comprises a spray adaptor adapted to communicate with the bore of the body and defining a distal outlet. The spray adaptor comprises a first gas passageway cooperatively associated with the distal outlet. The first gas passageway is configured to direct gas to create a spray discharge of the sealant. Tubing is in fluid communication with the first gas passageway and is adapted to be placed in fluid communication with the first gas outlet. An actuating member is adapted to be cooperatively associated with the pusher member. The actuating member is configured to generate the supply signal during movement of the pusher such that gas is supplied from the first gas outlet in at least partial dependence on the signal.

According to another aspect of the invention there is provided an applicator assembly for applying a sealant to a work surface, the applicator assembly comprising; a first apparatus comprising an elongated body defining an interior bore for containing sealant and having proximal and distal ends, a piston movably positioned in the bore, and a pusher member operatively associated with the piston extending through the proximal end of the bore; a gas supplying device having a first gas outlet, a supply signal input to receive a supply signal, a switch to actuate a flow of gas to the first gas outlet, and a control mechanism to cooperatively associate the switch and a signal supplied to the supply signal input; and a second apparatus comprising a spray adaptor and an actuating member; the spray adaptor being in communication with the bore of the body and defining a distal outlet, the spray adaptor comprising a first gas passageway cooperatively associated with the distal outlet, the first gas passageway configured to direct gas to create a spray discharge of the sealant; tubing in fluid communication with the first gas passageway and in fluid communication with the first gas outlet; the actuating member being cooperatively associated with the pusher member, the actuating member being configured to generate the supply signal during movement of the pusher member such that gas is supplied from the first gas outlet in at least partial dependence on the signal.

According to another aspect of the invention there is provided an applicator assembly for applying a sealant to a work surface, the applicator assembly comprising; a first apparatus comprising an elongated body defining an interior bore for containing sealant and having proximal and distal ends, a piston movably positioned in the bore, and a pusher member operatively associated with the piston extending through the proximal end of the bore; a gas supplying device having a first gas outlet, a supply signal input to receive a supply signal, a switch to actuate a flow of gas to the first gas outlet, and a control mechanism to cooperatively associate the switch and a signal supplied to the supply signal input; and a second apparatus comprising a spray adaptor and an actuating member; the spray adaptor being adapted to communicate with the bore of the body and defining a distal outlet, the spray adaptor comprising a first gas passageway cooperatively associated with the distal outlet, the first gas passageway configured to direct gas to create a spray discharge of the sealant; tubing in fluid communication with the first gas passageway and adapted to be placed in fluid communication with the first gas outlet; the actuating member adapted to be cooperatively associated with the pusher member, the actuating member being configured to generate the supply signal during movement of the pusher member such that gas is supplied from the first gas outlet in at least partial dependence on the signal.

According to another aspect of the invention there is provided an apparatus for use in an applicator assembly for applying a sealant to a work surface; the apparatus comprising an elongated body defining an interior bore for containing sealant and having proximal and distal ends, a piston movably positioned in the bore, and a pusher member operatively associated with the piston extending through the proximal end of the bore, wherein the pusher member is adapted to be cooperatively associated with an actuating member of the applicator assembly.

According to another aspect of the invention there is provided an apparatus for use in an applicator assembly for applying a sealant to a work surface; the apparatus comprising a spray adaptor and an actuating member; the spray adaptor being adapted to communicate with a bore of a body of the applicator assembly and defining a distal outlet, the spray adaptor comprising a first gas passageway cooperatively associated with the distal outlet, the first gas passageway configured to direct gas to create a spray discharge of the sealant; tubing in fluid communication with the first gas passageway and adapted to be placed in fluid communication with a first gas outlet of a gas supplying device; the actuating member being adapted to cooperatively associate with a pusher member of the body, the actuating member being configured to generate a supply signal to the gas supplying device during movement of the pusher member such that gas is supplied from the first gas outlet in at least partial dependence on the signal.

According to another aspect of the invention there is provided a kit for use in an applicator assembly for applying a sealant to a work surface; the kit comprising a first apparatus and a second apparatus; the first apparatus comprising an elongated body defining an interior bore for containing sealant and having proximal and distal ends, a piston movably positioned in the bore, and a pusher member operatively associated with the piston extending through the proximal end of the bore, wherein the pusher member is adapted to be cooperatively associated with an actuating member of the second apparatus; and, the second apparatus comprising a spray adaptor and an actuating member; the spray adaptor being adapted to communicate with the bore of the body and defining a distal outlet, the spray adaptor comprising a first gas passageway being adapted to cooperatively associate with the distal outlet, the first gas passageway configured to direct gas to create a spray discharge of the sealant; tubing in fluid communication with the first gas passageway and adapted to be placed in fluid communication with a first gas outlet of a gas supplying device; the actuating member being configured to generate a supply signal to the gas supplying device during movement of the pusher member such that gas is supplied from the first gas outlet in at least partial dependence on the signal.

This summary is not intended as an exhaustive identification of each aspect or feature of the present invention that is now or may hereafter be claimed, but represents a summary of certain aspects of the present invention to assist in understanding the more detailed description that follows. Additional aspects or features of the present invention may be set forth in the following description.

Although described later in terms of certain structures, it should be understood that the system and apparatuses of the present invention are not limited to the identical structures shown. It should be understood that the structures described and claimed are intended to have a broad interpretation that includes all of the more specific structures, such as those mentioned above, in which it may find commercial application.

BRIEF DESCRIPTION OF THE DRAWINGS

FIG. 1 is a top perspective view of an apparatus, with portions of the apparatus being shown as transparent to aid illustration, and also includes a sealant applicator assembly, a control unit, and a gas supply source, shown schematically.

FIG. 2 is a back perspective view of the control unit shown in FIG. 1.

FIG. 3 is an enlarged top perspective view of the apparatus shown in FIG. 1.

FIG. 4 is a partial enlarged top perspective view of the proximal end of the apparatus shown in FIG. 1.

FIG. 5 is a bottom perspective view of the apparatus shown in FIG. 1.

FIG. 6 is a front perspective view of an actuating member of the apparatus.

FIG. 7 is a back perspective view of the actuating member.

FIG. 8 is a top view of the apparatus in FIG. 1.

FIG. 9 is a side view of the apparatus shown in FIG. 1.

FIG. 10 is a partial enlarged bottom view of the proximal end of the apparatus shown in FIG. 1.

FIG. 11 is a front view of a pusher member shown in FIG. 1.

FIG. 12 is a sectional view along line 12-12 of FIG. 11.

FIG. 13 is a rear view of the pusher member.

FIG. 17 shows a modified spray adaptor in which gas mixes with one of the sealant components.

FIG. 18 shows another modified spray adaptor in which gas separately mixes with each of the sealant components.

FIG. 19 shows yet another modified spray adaptor in which gas mixes with both of the sealant components after the components are mixed together.

FIG. 20 is a top perspective view of an alternative actuating member, with portions of the apparatus being shown removed to aid illustration.

FIG. 21 is a right side perspective view of the actuating member shown in FIG. 20.

FIG. 22 is a left side perspective view of the actuating member shown in FIG. 20.

FIG. 23 is a top view of the actuating member shown in FIG. 20.

FIG. 23A is a cross-sectional view taken along plane 23A shown in FIG. 23.

FIG. 24 is a rear view of the actuating member shown in FIG. 20.

FIG. 31 is a top perspective view of an alternate embodiment of an apparatus of the present invention, with portions of the apparatus being shown removed to aid illustration.

FIG. 32 is a top perspective view of a yet further embodiment of an apparatus of the present invention.

DESCRIPTION OF THE PREFERRED EMBODIMENTS

Figure 14:
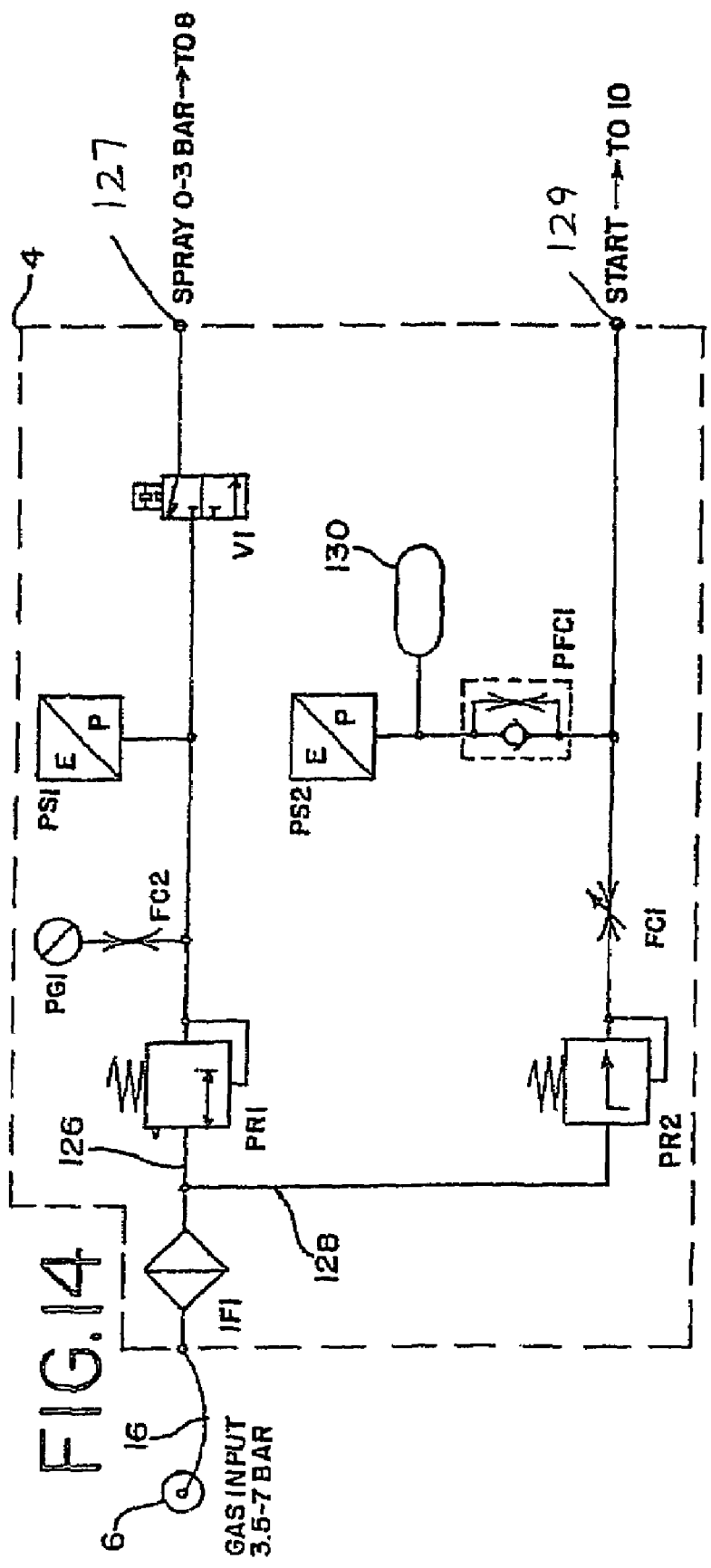
FIG. 14 is a pneumatic diagram of the control unit shown in FIG. 1.

In accordance with one aspect of the present invention, FIG. 1 generally illustrates a system for applying sealant, such as tissue sealant, to a work surface, such as biological tissue. The system preferably includes a tissue sealant apparatus, generally indicated at 2, a control unit, generally indicated at 4, and a pressurized, sterile gas or air supply source, generally indicated at 6. Each of these structures will be described in further detail below in accordance with various aspects of the invention.

In FIG. 1, the tissue sealant apparatus 2 includes a distal end, generally indicated at 12, and a proximal end, generally indicated at 14. The apparatus 2 is preferably connected to the control unit 4 by first and second gas passageways 8 and 10, respectively, which may be formed, at least in part, by tubing which preferably connects the control unit 4 and the apparatus 2. Generally, the first gas passageway 8 is associated or fluidly communicates with the distal end 12 of the apparatus and the second passageway 10 is associated with or fluidly communicates with the proximal end 14. Ends 15 of the tubing may have different shaped ends, such as male or female type connectors, where they are attached to the control unit 4 so as to allow for removable connection of the tubing to the control unit and prevent improper loading of the tubing on the control unit. The apparatus 2 is preferably constructed so that it may be easily disposed of after use.

The control unit 4 is preferably connected to the gas supply source 6 using a supply passageway 16 which extends from the control unit 4. It is also possible that the gas supply source 6 may be incorporated integrally with the control unit 4. The control unit 4 preferably supplies gas to one or both of the gas passageways 8 and 10, and which will be described in further below. The supply of gas may have a pressure range of approximately 3.5 to 7 bar, although other ranges are also possible. The control unit 4 further may include a pressure control knob 18 for manually controlling the pressure of gas supplied to the apparatus through at least one of the first and second gas passageways 8 and 10 and preferably the first gas passageway 8. A pressure gauge 20 may allow for visible monitoring of the pressure of the gas in the first gas passageway 8 to facilitate the setting of the desired pressure. In a preferred embodiment, the desired pressure ranges from 0.1 to 3 bar and the pressure gauge may indicate pressures from 0.0 to 4.0 bar.

As shown in FIG. 2, the rear surface of the control unit 4 may include a horizontally-disposed clamping member 22 and/or a vertical-disposed clamping member 24 having a biasing member 26 to assist attachment of the control unit to a table, rod, pole or other horizontally or vertically-disposed clamping surfaces during use.

In a further aspect of the present invention, the apparatus 2 of FIG. 1 generally includes an elongated body 28 having a proximal end, generally indicated at 27 and a distal end, generally indicated at 29. By way of example and not limitation, FIGS. 1 and 3 show the elongated body 28 defining two interior bores 30 and 32, for example, an apparatus of the type having a double-barrel syringe applicator where each barrel contains a tissue sealant component. Each bore 30 and 32 is adapted to contain a component of the tissue sealant. For example, each bore may contain one of fibrinogen or thrombin or other like tissue sealant components. The illustrated structure is shown by way of example and not limitation and it is realized that other structures are also possible. For example, the apparatus may employ alternative structures, such as single and multiple interior bores, and such structure may depend on the type of sealant employed.

As shown in FIG. 3, a frame 34 preferably carries the interior bores 30 and 32 within a corresponding cavity 36 and 38 so that the interior bores extend along an axis parallel to each other. The frame 34 may also define slots 40 and 42, shown in FIG. 3, at a proximal end of the frame in which a flanged end 44 and 46 of the corresponding bore 30 and 32 is received. A piston 48 and 50 is movably positioned in each respective interior bore 30 and 32.

A pusher member, generally indicated at 52, is operatively associated with the pistons 48 and 50 and includes plunger members 53 and 54 that extend through the proximal end of each bore 30 and 32 corresponding to each piston 48 and 50. Movement of the pusher member 52 toward the distal end 12 of the apparatus 2 simultaneously moves the pistons 48 and 50 to eject the tissue sealant contained therein. As shown in FIGS. 8 and 9, an extension arm 56 may be provided which extends proximally from the frame 34 parallel to the plunger members 53 and 54 to a proximal platform 58 of the pusher member 52 and is slidably attached to the frame to allow for movement of the pusher member 52 relative to the body 2. In FIGS. 3-4, a flanged end 60 and 62 of each respective plunger member 53 and 54 may be received in a corresponding slot 64 and 66 (.also shown in FIGS. 12-13) defined in a distal surface 68 of the proximal platform 58, so as to synchronize the movement of the plunger members 53 and 54 by pressing on the pusher member 52. In an alternate embodiment, the pusher member 52 may be comprised of integrally attaching the plunger members 53 and 54 with proximal platform 58.

As shown in FIGS. 10-12, the pusher member 52 is provided with a proximal surface 70 which includes two ridges 72 spaced from one another extending from a bottom edge 76 to a top edge 78 of the pusher member 52. As shown in FIGS. 11 and 12, a ramp 74 is preferably positioned on each ridge 72 and is spaced between the top and bottom edges 76 and 78. In FIG. 12, the ramp 74 forms an inclined surface which extends from a recessed edge 79 defined near the bottom edge 76 to a notch 80 defined near the top edge 78. Preferably, each ramp 74 is inclined at a 2° angle from the recessed edge 79 to the notch 80. As shown in FIGS. 10 and 11, two channels, grooves or the like 82 and 84 are preferably formed in the proximal surface 70 in the valley defined between the ridges 72. The channels 82 and 84 extend into the proximal surface 70 in a distal direction at an oblique angle, as best shown in FIG. 10.

Turning to FIGS. 4-5, an actuating member, generally indicated at 86, is cooperatively associated with the pistons 48 and 50 to eject sealant. By "cooperatively associated" it is meant that the actuating member may be part of the structure that actuates the ejection the sealant or the actuating member may be operatively attached to or carried by such structure or may be separate from the structure but interactive directly or indirectly with such structure. In FIGS. 4-5, the actuating member is preferably removably carried by or mounted to the pusher member 52. It is also possible for the actuating member to be formed integrally with the pusher members (as shown in FIGS. 22-31) and/or with other elements of the apparatus (as shown in FIG. 32). In FIGS. 4-5, the actuating member is connected to the proximal end of the pusher member 52 although other locations are also possible.

The actuating member is also operative to actuate a supply of gas to create a spray discharge, simultaneously with the ejection of tissue sealant. It is contemplated that the actuating member may be operable to actuate a spray discharge in a variety of ways. Actuation by the actuating member may be provided by air, pressure, electricity and other mechanisms. By way of example and not limitation, it is possible that the actuating member may be operated for actuation by an electrical switch or the like. Actuation may also be triggered by a variation in a control gas pressure, either by an increase or decrease. This description is not exhaustive of the techniques which may be employed to create actuation of a spray discharge and it is realized that other variations are possible in addition to those discussed herein.

Preferably, the actuating member comprises a second gas passageway that includes an opening which permits gas flow. The second gas passageway may be placed in fluid communication with the supply signal input of the gas supply device. Upon user actuation of the actuation member to move the piston, the opening is restricted, generating the supply signal to the gas supplying device. In FIG. 6, the actuating member 86 preferably includes a proximal portion 88 which defines a user-contact surface and a distal portion 90 which attaches to the pusher member 52. Although the user-contact surface will be described by specific structures below, these are shown by way of example and not limitation. It is contemplated that the user-contact surface may be associated with a manually or electrically-actuated switch which causes a variation in gas or pressure or generates an electrical signal so as to actuate the supply of gas to the first gas passageway 8. It is also possible that the user-contact surface may be associated with different portions of the actuating member 86 other than the proximal portion 88.

In FIGS. 6-7, the proximal portion 88 preferably includes a depression 92 having a concave shape or configuration that is adapted to receive a user's finger, such as a thumb. The depression 92 may include a tubular protrusion 94 positioned in the depression 92 such that the user's finger generally contacts this protrusion 94 during ejection of tissue sealant. In FIG. 6, the protrusion 94 is preferably defined around an opening 96. As shown in FIG. 5, the actuating member 86 preferably forms a portion of the second flow passageway 10 and the opening 96 permits gas flow to or from the second gas flow passageway 10. Upon user actuation of the actuation member to move the piston, the opening is restricted, generating the supply signal to the gas supplying device. In FIG. 5, tubing which preferably defines another portion of the second flow passageway 10 fluidly communicates with the actuating member 86 by connection to a flow port 102 defined in the actuating member on one side thereof, as shown in FIG. 6. Although the positioning of the opening 96 and the flow port 102 are shown in FIGS. 5-7 on the proximal portion 88 and a side portion, respectively, of the actuating member 86, other variations are also possible.

As shown in FIG. 7, the actuating member 86 preferably defines two parallel ribs 98 and 99 extending from the distal portion 90. The ribs 98 and 99 may extend between the side edges 97 and preferably are generally symmetrical about a lateral line A. The actuating member 86 also preferably includes two angled projections 100 and 101 which are positioned between the ridges 98 and 99 and extend in a distal direction at an oblique angle. The projections 100 and 101 generally are symmetrical about a vertical line B. As shown in FIG. 10, each projection 100 and 101 is preferably shaped and angled to be received by the corresponding channels 82 and 84 such that the actuating member 86 is removably attached to the pusher member 52. Other fastening structures may be employed to connect the actuating member other than the structures shown and described. Further, attachment may be provided by a projection formed in the pusher member 52 which is received by the actuating member 86.

As shown in FIG. 10, the actuating member may be removably attached by slidably inserting the projections 100 and 101 into the corresponding channels 82 and 84. With reference also to FIG. 11, during insertion, the ribs 98 and 99 traverse the ridges 72 and ramps 74 until the leading rib 98 is received by the notches 80 and the following rib 99 engages the recessed edge 79. The projections 100 and 101 engage channels 82 and 84. The inclined surfaces of the ramps 74 preferably contact the leading rib 98 causing the actuating member to slightly flex in a leaf spring-like manner and provide increased resistance to movement as the incline increases. Such that, when the rib 98 slides past the ramps 74 and engages the notches 80 and rib 99 slides over the ridge 72 and engages the recessed edge 79, the user feels less resistance and, more preferably, feels a tactile sensation and possibly an aural indication. The actuating member 86 may be slidably removed by the user urging the rib 98 out of notch 80 and along the ramps 74 and moving the rib 99 out of the recessed edge 79. The ribs 98 and 99 preferably have sufficient flexibility to permit slidable insertion and removal. It is also possible to attach the actuating member to the pusher member 52 in an orientation 180 degrees rotated relative to orientation shown in the drawings, for example, where it is desired that the tubing may extend from the other side of the actuating member.

Turning to FIGS. 8 and 9, a spray adaptor 104 is provided that is preferably carried by or connected to the distal end 29 of the body. In FIG. 8, distal outlets 106 and 108 may be associated with the respective interior bores 30 and 32 of the body 28 to allow ejection of the sealant components and for communication with the spray adaptor 104. Respective sealant passageways 110 and 112 may be formed in the spray adaptor 104 to communication of sealant from the respective interior bores 30 and 32. The spray adaptor 104 may define separate outlets 114 and 116 for each sealant component, as shown in FIG. 8, or, alternatively, may allow ejection of a mixed component stream, as shown in FIG. 19, in which the mixture of the components is provided inside the spray adaptor 104. It is contemplated that the spray adaptor 104 in FIGS. 8 and 9 shown by way of example and not limitation, and other configurations are possible.

In FIG. 9, the spray adaptor 104 also preferably forms a portion of the first gas passageway 8 and preferably connects to the tubing that forms another portion of the first gas passageway 8. In FIGS. 8 and 9, the spray adaptor 104 defines a gas flow path 118 which communicates with a gas outlet 120. In FIGS. 8 and 9, a portion of the gas flow path 118 preferably has an annular or circular shape, although other shapes are also possible, such as, for example, oval, oblong, or the like. FIGS. 8 and 9 also show the gas outlet 120 disposed around the sealant outlets 114 and 116 although other variations are also possible including where a separate gas outlet is disposed around each sealant outlet. It is possible for the gas to mix with at least one of the sealant components either before or after the components are mixed together. In FIGS. 17-18, gas mixes with one of the sealants, as in FIG. 17, and or two sealants, as in FIG. 18, before the sealant components are mixed together and, in FIG. 19, gas mixes with an already mixed sealant upstream of a combined gas and sealant distal outlet. The operation of the actuating member 86 preferably provides a supply of gas to the spray adaptor 104 through the first gas passageway 8 simultaneously with the ejection of sealant.

In accordance with another aspect of the present invention, a sealant applicator assembly 122, as best shown in FIG. 1, is provided that includes a spray adaptor 104, a first gas passageway 8 and an actuating member 86, as shown and described above. These structures of the sealant applicator assembly preferably are attached to one another in the configuration shown in FIG. 1, and may be sold as a disposable set for use with a double-barrel syringe plunger structure for ejecting tissue sealant, similar to the syringe plunger structure shown and described above, or other like structures. The spray adaptor and actuating member of the sealant applicator assembly are preferably removably attached to the appropriate locations of the syringe plunger structure, similar to the above description. By way of example and not limitation, the syringe plunger structure may be used and adapted for use with other sealant applicator assembly disposable sets which contain other adaptors, such as a catheter or cannula, or other adaptors for that provide a spray or non-spray discharge of tissue sealant. It is also possible for the syringe plunger structure to be included with the sealant applicator assembly as a combined disposable set.

Figure 15:
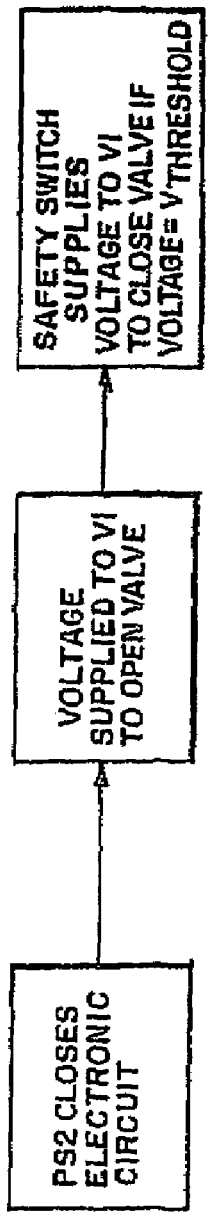
FIG. 15 is a flow chart of an electrical circuit employed in the control unit.
Figure 16:
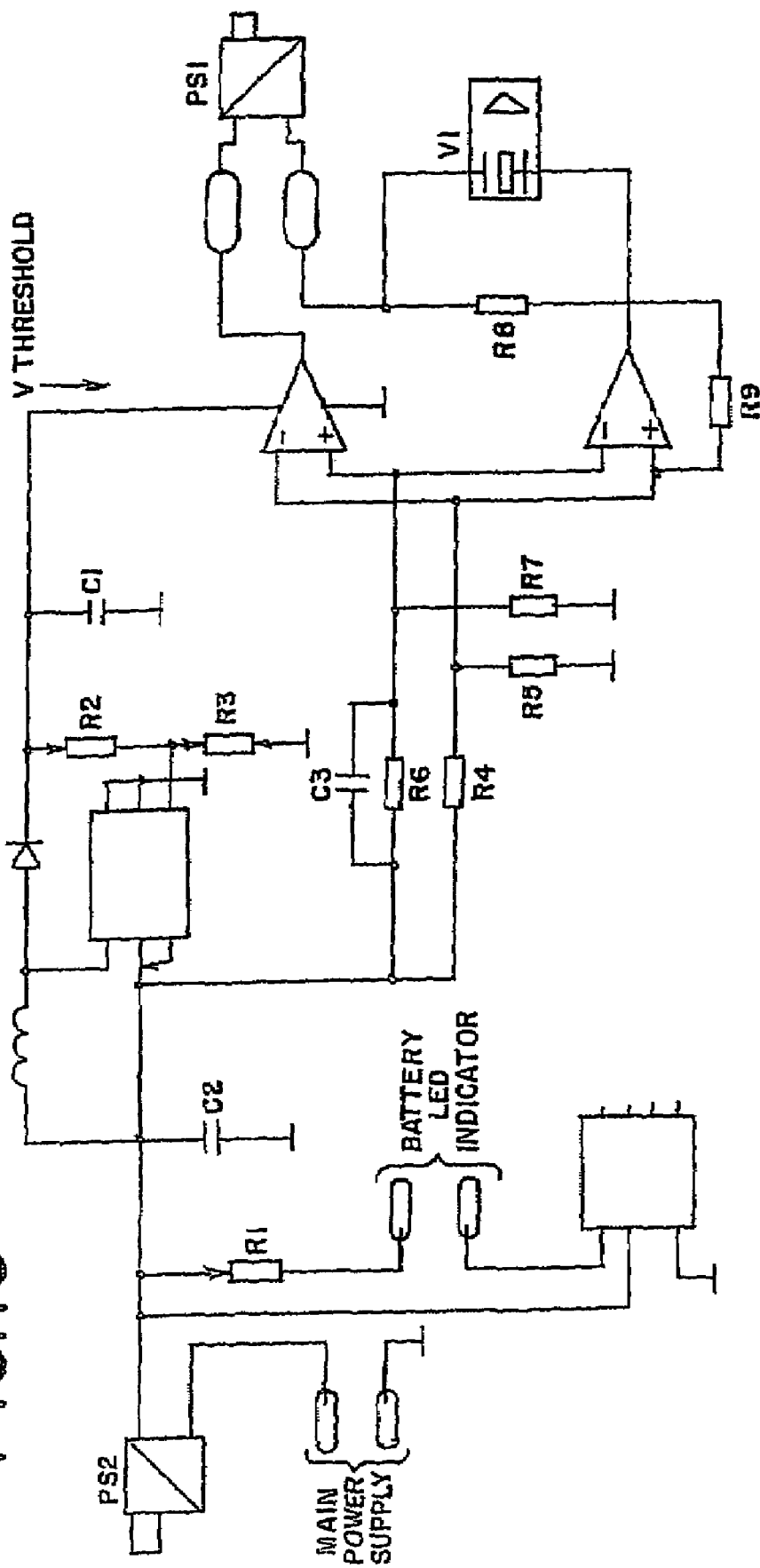
FIG. 16 is a schematic of an electrical circuit employed in the control unit.
Figure 25:
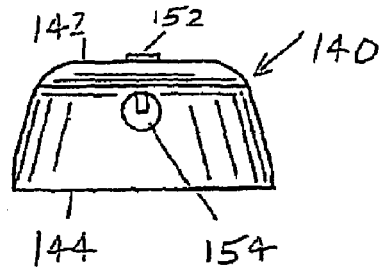
FIG. 25 is a right side view of the actuating member shown in FIG. 20.
Figure 26:
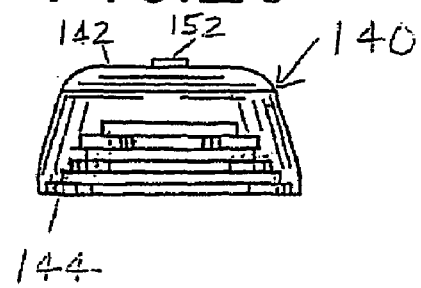
FIG. 26 is a left side view of the actuating member shown in FIG. 20.

In accordance with a yet further aspect of the present invention, the control unit 4 may be provided for use with any of the described system and apparatuses. As shown in FIG. 1, the control unit 4 is cooperatively associated with the apparatus to simultaneously activate the supply of gas with the ejection of tissue sealant. By way of example and not limitation, FIGS. 14-16 show an example of the control unit 4 which may be used to supply and control gas to the first and second gas passageways 8 and 10. It is contemplated that this description is not exhaustive and that modifications to the control unit 4 are possible and will depend on the structures employed to apply tissue sealant and how they are operated or actuated, such as for example, by pneumatic, electric, or other types of actuation techniques.

As shown in FIG. 14, the control unit 4 may be supplied by gas from the gas supply source 6 through a supply passageway 16. The incoming gas supply may be filtered by a filter IF1. The supply of gas may flow to a first flow branch 126 and a second flow branch 128. Each flow branch 126 and 128 preferably includes a corresponding pressure regulator PR1 and PR2. Each pressure regulator preferably is configured to monitor the pressure along its respective flow branch and may further be adjustable to accommodate variations in tubing, such as the inner diameter and length of such tubing.

In the first flow branch 126, the pressure of gas preferably is adapted for manual control and/or adjustment by the user by way of the pressure control knob 18, as shown in FIG. 1. In FIG. 14, a pressure gauge PG1, as also shown at 20 in FIG. 1, and a flow controller FC2 may also be provided to monitor the pressure, which preferably may be in the range of approximately 0 to 3 bars, and more preferably may be in the range of approximately 2 to 3 bars. In FIG. 14, the first flow branch 126 preferably includes an outlet 127 which is adapted for communication with the first flow passageway 8 so as to control the desired spray discharge pressure and further includes a pressure safety switch PS1 and a supply valve V1. The supply valve V1 may be normally biased to a closed position such that no gas is supplied to the first gas passageway 8 and, thus, no spray discharge is created. The pressure safety switch PS1 and supply valve V1 will be described in further detail below.

In FIG. 14, the second flow branch 128 may include a corresponding flow controller FC1 and preferably maintains a control gas pressure. The control gas pressure is preferably a predetermined pressure or pressure range, which may be set during the manufacturing process. The control gas pressure preferably is in the range of approximately 0.01-0.20 bar, and more preferably in the range of approximately 0.05-0.15 bar. With reference to FIGS. 4-5, the control gas pressure is preferably supplied through an outlet 129 (FIG. 14) to the second gas passageway 10 to exit the opening 96 defined in the actuating member 86. The control gas pressure is preferably sufficient to provide a tactile sensation to the user's finger so as to indicate to the user when such finger is positioned over the opening 96. Alternatively, it is also possible for the control gas pressure to be maintained under conditions such that gas does not exit the opening 96.

As shown in FIG. 14, the control unit 4 further preferably comprises a pressure switch PS2 which communicates with the flow branch 128. The pressure switch PS2 is preferably operably associated with the supply valve V1 which communicates with the other flow branch 126. The pressure switch PS2 is operable to open the supply valve V1 such that gas is supplied to the first gas passageway 8 thus providing a spray discharge of tissue sealant. The pressure switch PS2 preferably activates to open the valve in response to receiving a control signal from the apparatus. The control signal is created when the user-applied force is supplied to eject tissue sealant.

The user-applied force simultaneously causes a variation in pressure. Such user-applied force preferably restricts or occludes the exit of gas from the opening 96 so as to prevent gas from exiting the opening and cause an increase in pressure sufficient for the control signal to be received by the pressure switch. Alternatively, in an alternate embodiment, it is possible that the user-applied force may trigger a decrease in pressure if the user-applied force allows gas to be released from the opening which otherwise does not exit the opening 96. The pressure switch PS2 preferably monitors for such variation in pressure in the second gas passageway 10 and activates to open or close the valve in response to such variation in pressure. The resulting spray discharge provides a combined gas and tissue sealant spray from the distal end of the apparatus 2. When the user-applied force is removed, the ejection of tissue sealant may stop immediately, or, alternatively, the supply of gas may be stopped after a predetermined time delay.

As shown in FIG. 14, a timing delay control member PFC1 may be operatively connected to the control unit 4, such as the pressure switch PS2. The timing delay control member PFC1 preferably prevents the pressure switch PS2 from closing the valve for a predetermined period of time after the user applied force is removed. In FIG. 14, the timing delay control member PFC1 preferably communicates with the flow passageway 118 (shown in FIGS. 8-9) and may utilize additional tubing 130. Preferably, the time delay is within the range of approximately 0.1 seconds to 0.9 seconds and, more preferably, approximately 0.5 seconds. The time delay provides a discharge of gas after the user has stopped the ejection of tissue sealant. The additional gas discharge may be helpful in dislodging any remaining tissue sealant from the distal end of the apparatus so as to prevent clogging or fouling of the distal end.

As further shown in FIG. 14, a pressure safety switch PS1 may communicate with the flow passageway 126 and provided for overpressure protection. The pressure safety switch preferably prevents the pressure of the supply of gas to the apparatus from exceeding a predetermined threshold level. When the threshold level is reached, the supply of gas to the distal end of the apparatus may be automatically shut off.

FIGS. 15 and 16 illustrate a flow chart and schematic of an electrical circuit which may be used in connection with the operation of the pressure switch PS2 and the supply valve V1, as described above. As shown in FIG. 16, the pressure switch PS2 is connected to a main power supply, such as a battery. A battery LED indicator may be used to indicate when the battery is running out of the necessary charge. As shown in FIGS. 15 and 16, the activation of the pressure switch PS2 closes the electronic circuit so as to supply voltage to the valve V1, thus, opening the valve V1. In FIG. 16, the voltage which is supplied to the valve V1 is compared to a predetermined threshold voltage $V_{THRESHOLD}$. If the voltage exceeds the threshold voltage $V_{THRESHOLD}$, then the pressure safety switch PS1 overrides the pressure switch PS2 and closes the valve V1.

The pusher member may be integral with the actuating member. Alternatively, the pusher member may be separate from and adapted to be cooperatively associated with the actuating member. An alternative embodiment of an actuating member, generally indicated at 140, is shown in FIGS. 20-30 for use with an apparatus similar to the apparatus described in FIGS. 1-16. Such embodiment is similar to the embodiment described in FIGS. 6-7, except that the embodiment in FIGS. 20-30 includes an actuating member.140 which is formed as an integral part of the pusher member or members that are associated with a conventional syringe piston construction. Accordingly, those portions of the apparatus which are identical to those portions in FIGS. 1-16 will not be repeated.

In FIGS. 20-30, the actuating member 140 includes a proximal or top portion 142 which defines a user-contact surface and a distal portion or underside 144 which attaches to plunger members 146 and 148 of the syringe(s). In FIG. 23A, the actuating member 140 may define a gas passageway 150 which extends between first and second ends 152 and 154. The first end 152 may be defined in the user contact surface 142 (as shown in FIGS. 20-24) and the second end 154 of the passageway 150 may be defined along a side edge of the actuating member extending between the proximal and distal portions 142 and 144 (or top side and underside, respectively) (see FIGS. 21, 23A and 25 or elsewhere that is convenient). With reference to FIG. 20, the second end 154 of the passageway 150 preferably communicates via tubing 156 to a control unit and gas or pressure source (such as indicated at 4 and 6 in FIG. 1).

In FIGS. 20-24, the proximal portion or user-contact surface 142 has a contoured surface different than that shown in FIGS. 1-13. Although other contours are also possible, and the present application is not limited to the contoured surfaces shown herein, the proximal portion 142 in FIGS. 20-24 preferably includes a raised central portion 158 in which the first end 152 of the passageway 150 may be defined and concave portions 160 which extend to each side of the raised portion 158. As shown in FIG. 24, the first end 152 of the passageway 150 may terminate slightly above the raised portion 158 so that the user may determine the location of the first end 152 based on tactile feel. Alternatively, for example, the first end 152 may be recessed or flush with the raised portion 158.

Figure 27:
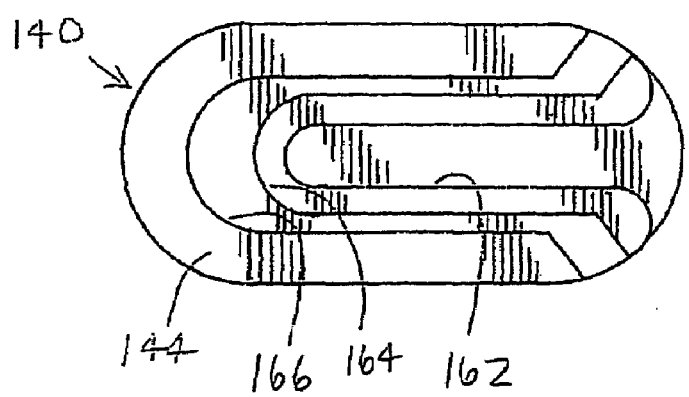
FIG. 27 is a bottom view of the actuating member shown in FIG. 20.
Figure 28:
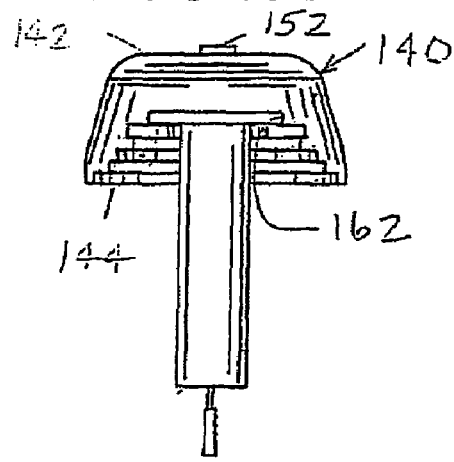
FIG. 28 is a view similar to FIG. 26 further including a plunger member associated with the actuating member.
Figure 29:
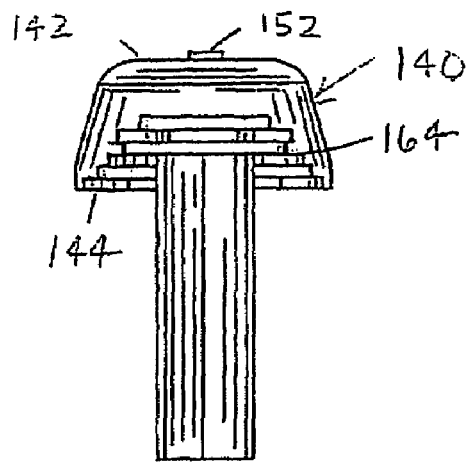
FIG. 29 is a view similar to FIG. 28 except that it includes a different plunger member having a larger diameter size than that shown FIG. 28.
Figure 30:
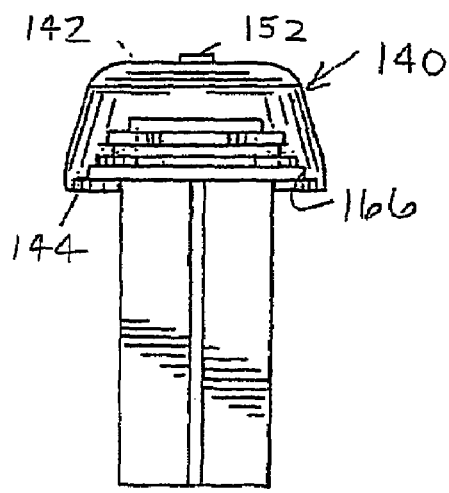
FIG. 30 is a view similar to FIG. 29 except that it includes an alternate plunger member having a larger diameter size than shown in FIG. 29.

As shown in FIGS. 22, 23A and 26-30, the distal portion or underside 144 includes laterally disposed slots 162, 164 and 166 for receiving plunger members 146 and 148 having differently sized flanged ends. As best seen in FIGS. 28-30, small, medium and large diameter-sized flanged ends may be received in correspondingly-sized slots 162, 164 and 166. The size of the flange is typically different for different size (volume) syringes. This allows one actuator to accommodate different syringe sizes (volumes) that may be needed for different procedures. As shown in FIG. 27, each of the slots 162, 164 and 166 may be sized and configured to receive a single plunger member or a pair of plunger members oriented in a side-by-side relationship.

In accordance with the above described invention, the embodiment of FIGS. 20-30, may be associated with the control unit 4 (as shown in FIG. 1) to supply and control gas from a gas source. In FIGS. 20-30 the gas passageway 150 is occluded by the user when the user's thumb is placed over the second opening 152 formed in the user-contact surface 142. In accordance with previously described embodiments, the gas passageway 150 may fluidly communicate with the control unit and/or gas or pressure source (e.g., indicated at 4 and 6 in FIG. 1) via tubing 156 connected to the second end 154 of the gas passageway 150. In FIG. 20, such connection may be achieved by attaching an end of the tubing 156 having a projection or hook 168 which engages a behind a ramped detent or lug 170 on the user contact surface 142. Other types of fastening structures are also possible and are not limited to those shown and described. In accordance with the invention described above, when the second opening 152 is occluded by the user, a supply of gas is preferably supplied to the distal end of the applicator via appropriate tubing (e.g. as indicated at 8 in FIG. 1).

In FIG. 31, an apparatus, indicated generally at 172, includes an actuating member 174 which is also combined with the pusher member, similar to the previously described embodiments, and includes a top side or user-contact surface 176 having a contour similar to that shown in FIGS. 1-13 and a distal or underside portion 178. Similar to the embodiment shown in FIGS. 1-13, the embodiment in FIG. 31 includes a frame 180 having a slidable extension arm 182 and includes a pair of adjacent hollow cavities 184 and 186. The cavities 184 and 186 receive respective cylindrical bores (not shown) containing tissue sealant components. The distal portion (or underside) 178 of the actuating member 172 preferably includes tow slots 190 and 192 which each slidably receives a flanged end of a plunger member extending proximally from each fluid-containing bore disposed in respective cavities 184 and 186.

FIG. 32 shows an alternate tissue sealant apparatus, indicated generally at 200. Such apparatus is shown having a conventional gun-type applicator construction, although other constructions are also possible. The apparatus 200 generally defines a body 202 and a handle 204. The body 202 defines respective cavities for receiving fluid-filled cylindrical bores 206 having respective plunger members 208 extending therefrom. Each proximal end of the plunger member 208 is received by a pusher member 210. An actuating member, generally indicated at 212, is preferably operatively associated with the pusher member 210. The actuating member 212 includes a lever 214 which may be distally located and pivotally movable relative to the handle 204. The lever 214 may be operatively connected to the pusher member 210 by a drive mechanism shown and described in U.S. Pat. No. 6,585,696, which is assigned to Baxter International Inc., the assignee of the present application, and which patent is incorporated herein by reference. Accordingly, such mechanism need not be described further.

In FIG. 32, the lever 214 is preferably pivotally connected to the handle 204. The lever 214 may be pivoted in a direction towards and/or away from the handle 204 for actuation. The lever 214 also preferably defines at least a portion of a gas passageway 216. A first end or opening 218 of the passageway 216 is preferably defined in a distal portion of the lever 214. To activate the supply of tissue sealant, the user may cover or occlude the first end 218 of the passageway 216, such as with an index finger. A second end 220 of the passageway 216 preferably connects to a supply of gas via tubing 222 which preferably defines another portion of the gas passageway 216 so as to provide gas or pressure to the passageway 216. A supply of gas is also preferably supplied to the distal end of the apparatus 200 via appropriate tubing 224.

During operation of the apparatus 200 in FIG. 32, the lever 214 pivotally moves to eject tissue sealant from the bores 206 through the spray end 226 of the device. Gas or pressure may be simultaneously supplied to the spray end 226 through tubing 224 upon occlusion of the opening 218 formed in the lever 214, in accordance with the above described invention. The supply of gas may be stopped, either immediately or with a time delay, when the user stops occluding the opening 218, also in accordance with the above described invention.

As can be seen from the above description, the present invention has several different aspects, which are not limited to the specific structures shown in the attached drawings. Variations of these structures may be embodied in other structures for carrying out application of tissue sealant.

The invention claimed is:

1. A sealant applicator assembly for use with an apparatus of the type having an elongated body defining an interior bore for containing sealant component and having proximal and distal ends, a piston movably positioned in the bore, and a pusher member attached to the through the proximal end of the bore and cantilevered from the piston, the sealant applicator assembly comprising;
   a spray adaptor adapted to communicate with the bore of the body and defining a distal outlet;
   a first gas passageway cooperatively associated with the distal outlet, the first gas passageway configured to direct gas to create a spray discharge of the sealant; and
   an actuating member adapted to be cooperatively associated with the pusher member and that the entirety of which rides with the pusher member toward the distal end of the body to eject sealant through the distal outlet, the actuating member being operative to simultaneously actuate a supply of gas to said first gas passageway for creating a spray discharge of sealant.

2. The sealant applicator assembly of claim 1 further comprising a gas outlet surrounding the distal outlet and communicating with the first gas passageway.

3. The sealant applicator assembly of claim 1 wherein the actuating member includes at least a portion of a pusher member that is formed integrally with the actuating member.

4. The sealant applicator assembly of claim 1 wherein the actuating member is adapted to be removably carried by the pusher member.

5. The sealant applicator assembly of claim 1 further comprising a sealant passageway extending between said bore and said distal outlet and wherein the first gas passageway communicates with the sealant passageway upstream of the distal outlet.

6. The sealant applicator assembly of claim 1 wherein one portion of the first gas passageway is defined by the spray adaptor and another portion of the first gas passageway is defined by tubing which is connected to the spray adaptor.

7. The sealant applicator assembly of claim 1 further comprising a second gas passageway which is adapted for communication with a gas source, a portion of the second gas passageway being defined by the actuating member and including an opening that is varied by user actuation of the actuating member.

8. The sealant applicator assembly of claim 7, in which the opening in the second gas passageway is defined in a user-contact surface of the actuating member such that upon user contact with the actuating member to move the piston, the opening in the second gas passageway is restricted.

9. The sealant applicator assembly of claim 1 wherein the assembly further includes an elongated body defining an interior bore for containing sealant and having proximal and distal ends, a piston movably positioned in the bore, and a pusher member attached to the piston through the proximal end of the bore.

10. The sealant applicator assembly of claim 1 wherein the actuating member is operable to generate a control signal, the assembly further including a control unit operable upon receipt of the control signal to activate a flow of gas in communication with the first gas passageway to create a spray discharge of sealant.

11. An apparatus for applying a sealant to a work surface, the apparatus comprising:
   an elongated body defining an interior bore for containing sealant and having proximal and distal ends,
   a piston movably positioned in said bore;
   a pusher member attached to the piston through the proximal end of the bore and cantilevered from the piston;
   a distal outlet communicating with the bore;
   a first gas passageway cooperatively associated with the distal outlet, the first gas passageway configured to direct gas to create a spray discharge of the sealant; and
   an actuating member cooperatively associated with the pusher member that the entirely of which rides with the pusher member toward the distal end of the body to eject sealant through the distal outlet and is operative to simultaneously actuate a supply of gas to said first gas passageway, thereby creating the spray discharge of sealant for application to the work surface.

12. The apparatus of claim 11 wherein the actuating member is removably carried by the pusher member.

13. The apparatus of claim 11 wherein the actuating member is formed integrally with at least a portion of the pusher member.

14. The apparatus of claim 11 wherein the elongated body defines a plurality of parallel interior bores, each bore including a piston movably positioned in the bore, the actuating member being cooperatively associated with each piston for moving each piston simultaneously toward the distal end of the body.

15. A system comprising:
   an apparatus including an elongated body defining an interior bore for containing a sealant component and having proximal and distal ends, a piston moveably positioned in the bore, a pusher member attached to the piston through the proximal end of the bore and cantilevered from the piston, a distal outlet communicating with the bore, a first gas passageway cooperatively associated with the distal outlet and configured to direct gas to create a spray discharge of sealant, and an actuating member that is cooperatively associated with the pusher member and that the entirety of which rides with the pusher member toward the distal end of the body; and a control unit being operable upon receipt of a control signal from the actuating member to simultaneously actuate a flow of gas suitable for communication with the first gas passageway to create a spray discharge of sealant.

16. The control unit of claim 15 wherein the control unit is adapted to generate a control gas pressure for communicating with the actuating member through a second gas passageway, such that the actuating of the actuating member to move the piston varies the pressure in the second gas passageway, and the control member is adapted to activate said flow of gas in response to the variation in pressure in said second gas passageway.

17. The control unit of claim 15 wherein the control unit selectively controls a valve between a first condition in which gas is supplied to the first gas passageway from the gas source and a second condition in which no gas is supplied to the first gas passageway from the gas source.

* * * * *